United States Patent [19]

Fischell

[11] Patent Number: 4,724,830
[45] Date of Patent: Feb. 16, 1988

[54] FLOW CONTROL DEVICE FOR AN IMPLANTABLE PROSTHESIS

[76] Inventor: Robert E. Fischell, 1027 McCeney Ave., Silver Spring, Md. 20901

[21] Appl. No.: 832,407

[22] Filed: Feb. 24, 1986

[51] Int. Cl.[4] ............................................... A61F 2/26
[52] U.S. Cl. ..................................................... 128/79
[58] Field of Search ...................... 128/79; 251/335.2; 604/131, 141, 9

[56] References Cited

U.S. PATENT DOCUMENTS

| 2,348,388 | 5/1944 | Jenkins | 251/335.2 |
| 4,449,520 | 5/1984 | Palomar et al. | 128/79 |
| 4,559,931 | 12/1985 | Fischell | 128/79 |

FOREIGN PATENT DOCUMENTS 224990 5/1962 Austria ............................ 251/335.1

Primary Examiner—Gene Mancene
Assistant Examiner—Cary E. Stone
Attorney, Agent, or Firm—Fleit, Jacobson, Cohn & Price

[57] ABSTRACT

An elastomer diaphragm is mounted in a housing so as to be manually deflectable to open a valve mechanism and permit liquid flow in either direction through the housing between a pressurized reservoir and an implanted penile erection device. When pressure is removed, the diaphragm recovers to an original position and closes the valve mechanism with an inherent spring force. In a flaccid state, the valve mechanism also is retained closed by high liquid pressure on the reservoir side thereof. A push button on the diaphragm projects outward to make it easy to find under the skin of the user. The diaphragm is formed with integral seals, and is maintained in a compressed state to facilitate sealing of the liquid in the housing and to enhance the self-sealing capability of the diaphragm when penetrated by a needle.

21 Claims, 4 Drawing Figures

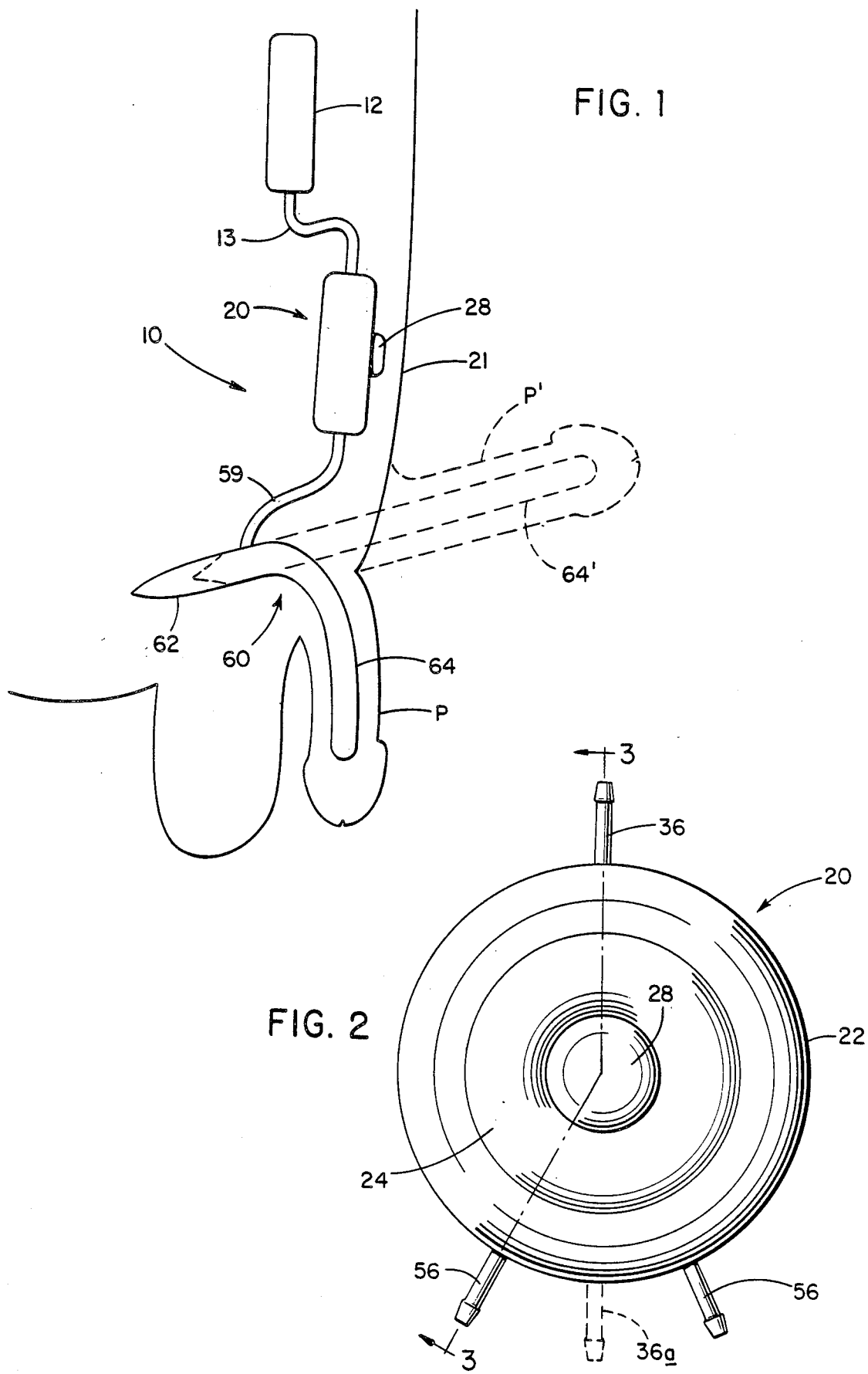

FLOW CONTROL DEVICE FOR AN IMPLANTABLE PROSTHESIS

BACKGROUND OF THE INVENTION

1. Field of the Invention

This invention relates to an improved flow control device for an implantable prosthesis and more particularly to an improved flow control device for an implantable penile erection device.

2. Description of the Prior Art

In my copending patent application, Ser. No. 526,893, filed Aug. 26, 1983 now U.S. Pat. No. 4,596,242, there is described a vapor pressure actuated penile erection device. That device utilizes a vapor pressure driven fluid that is stored in an implanted reservoir and released by the manual actuation, through the skin, of a subcutaneous flow control device. The released fluid actuates two hollow, fluid filled elastomer cylinders in the corpora cavernosa of a penis, causing the cylinders to expand and stiffen, thereby creating an erect state of the penis. A flaccid state of the penis is created by manual squeezing of the penis with one hand while simultaneously using the other hand to manually open the flow control device, thus driving the fluid back into the reservoir and thereby creating the flaccid state.

Although the flow control device described in my above-mentioned application operates satisfactorily, I now have developed a new and improved flow control device, which has been tested and actually used in human subjects. This flow control device forms the subject matter of this invention and has several significant operating and manufacturing advantages over the device described in my copending application.

SUMMARY OF THE INVENTION

In general, this invention relates to a flow control device for use with an implanted prosthesis and comprising an elastomer diaphragm disposed in an opening in a housing in fluid-tight relationship to an interior of the housing. A valve mechanism in the housing for controlling the flow of fluid through the housing includes a valve member mounted on the elastomer diaphragm for movement with the diaphragm from a closed position to an open position as the diaphragm is manually depressed in an inward direction, and for movement with the diaphragm back to a closed position as the diaphragm returns to an original condition when manual pressure on the diaphragm is removed.

More specifically, the housing is of annular construction and the elastomer diaphragm is disposed in a central opening of the housing and has an annular rim of reduced thickness mounted in an internal annular recess in the housing to form a fluid seal. An outwardly projecting push button having an annular head portion and a cylindrical shank portion of reduced diameter with respect to the head portion, is mounted on an outer side of the diaphragm with the head portion engaged with the outer side and with the shank portion extending through a central bore in the diaphragm. Passages formed in the housing permit flow of fluid through the housing from an inlet port to an outlet port thereof. The valve mechanism includes an "O"-ring seat and a valve poppet engageable with and disengageable from the "O"-ring. The valve poppet is secured to an inner side of the diaphragm by a screw extending through the valve poppet and threaded into the shank portion of the push button with the screw being threaded into the shank portion so as to compress the diaphragm and form a fluid seal. The construction of the diaphragm and the valve poppet is such that inherent spring force in the diaphragm and internal fluid pressure on the poppet combine to urge the poppet into a firmly closed position when the implanted prosthesis is in a deenergized state. The diaphragm also is provided with respective annular integral seals of semicircular cross section in the central bore and on the rim thereof, to facilitate sealing of fluid within the housing. The compressed diaphragm also has an enhanced self-sealing capability and may be penetrated by a non-coring hypodermic needle for adding or removing fluid from the housing.

It is an object of the present invention to provide a flow control device for an implantable prosthesis comprising an elastomer diaphragm which produces an inherent spring force to assure firm positive seating of a valve member against a valve seat of the device, thereby preventing inadvertent operation of the device.

Yet another object of the invention is to provide additional force for positive seating of the valve member against the valve seat during a flaccid or deenergized state as a result of a relatively high internal fluid pressure on one side of the valve member acting on a comparatively large area valve member.

A further object of the invention is to provide a flow control device wherein the elastomer diaphragm is of a construction which assures long term sealing of a fluid contained in the device.

It is another object of the invention to provide a flow control device wherein the elastomer diaphragm has an enhanced self-sealing capability and can also act as a septum and be penetrated by a hypodermic needle attached to a syringe for adding or deleting fluid from the device and an implanted prosthesis of which it forms a part.

A further object of the invention is to provide a flow control device having a projecting push button on a top surface of the device which can be readily felt under the skin of a user and hence can be reliably found and actuated to operate the device.

These and other objects of the invention, as well as many of the attendant advantages thereof, will become more readily apparent when reference is made to the following description, taken in conjunction with the accompanying drawings.

BRIEF DESCRIPTION OF THE DRAWINGS

FIG. 1 is a side view showing how a complete system for a penile prosthesis, utilizing the flow control device of the present invention, would be implanted in a human male.

FIG. 2 is a top view of the flow control device of the present invention.

DETAILED DESCRIPTION OF THE DRAWINGS

Figure 3:
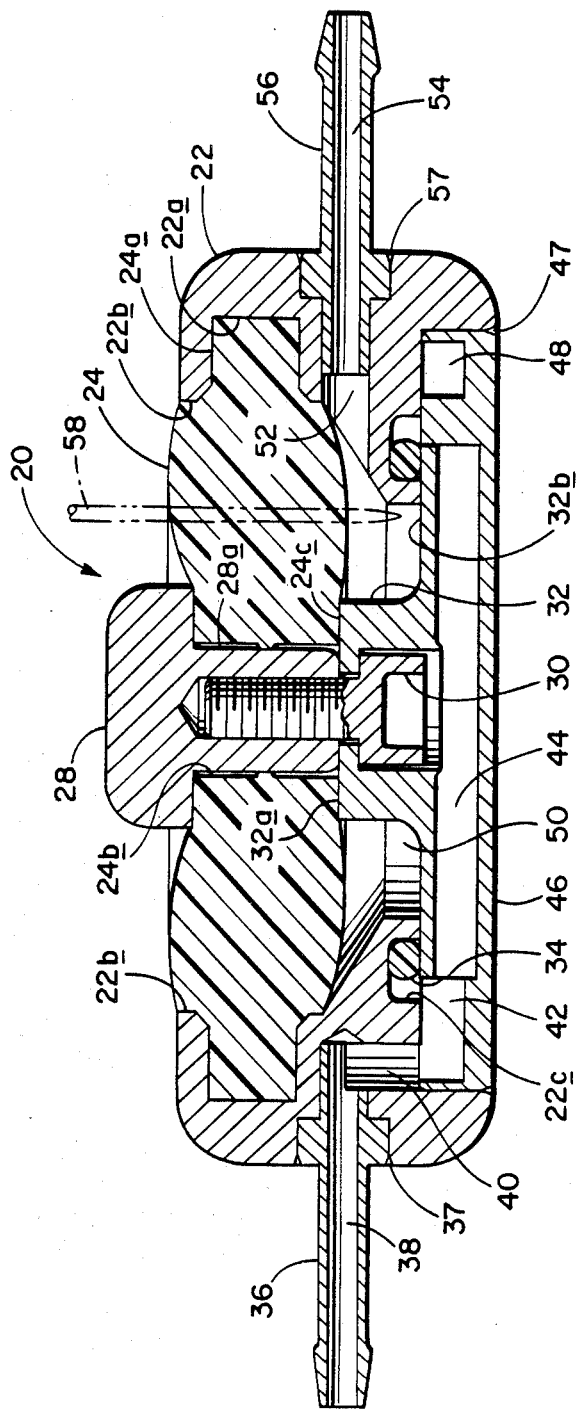
FIG. 3 is a cross-sectional view of the flow control device taken along the line 3—3 of FIG. 2.

FIG. 1 shows a side view of an implanted penile prosthesis 10 comprising a reservoir 12 which contains a vapor pressure driven fluid and which is described in detail in my copending application Ser. No. 526,893, the subject matter of which, to the extent not inconsistent with this disclosure, is hereby incorporated by reference. This fluid is typically a liquid in the form of normal saline solution and is hereinafter referred to as a "liquid".

In general, the pressure driven liquid will flow from the reservoir 12 thru a connecting tube 13 into a flow control device 20 of this invention, hereinafter referred to as the "actuator", when a valve in the actuator is opened by finger pressure being exerted upon skin 21 of the user at a location just above the center of the actuator, where a push button 28 of the actuator is located. The pressurized liquid then is driven through a connecting tube 59 into two hollow, elastomer stiffener cylinders 60 (only one shown) implanted in the corpora cavernosa of a penis P and each having a solid elastomer root 62 implanted in the user's body. This causes a pendulous portion 64 of the cylinders 60 to go from a flaccid (deenergized) state of the penis P (shown as solid lines in FIG. 1) to an erect state of the penis as shown at P' by dash lines in FIG. 1. The erect state P' occurs when the pendulous portion 64 is inflated as shown at 64'.

When the flaccid state of the penis P is desired, the penis, in its erect state P', is manually squeezed with one hand while simultaneously using the other hand to press through the skin 21 against the push button 28 of the actuator 20. When sufficient liquid is thus driven back into the reservoir 12, to obtain the flaccid state, the hand is removed from the push button 28, and then the manual pressure on the penis P is removed.

In this manner, the erect and flaccid states of the penis P can be readily created as desired by the man in whom the penile prosthesis 10 is implanted.

In FIG. 2 is shown a top plan view of the actuator 20, which comprises a main housing 22, an elastomer diaphragm 24, which preferably is relatively thick and which performs a multiplicity of functions as will be described herein, the centrally located push button 28, an inlet port 36 and two identical outlet ports 56. Although two outlet ports 56 are shown, the actuator 20 could operate with only a single outlet port. Further, while the disclosed arrangement of the inlet port 36 and the outlet ports 56 on opposite sides of the actuator 20 is convenient, it may also be desirable to locate the single inlet port on the same side of the actuator as the two outlet ports, and between the two outlet ports, as shown by the dash lines 36a of FIG. 2.

FIG. 3, which is a cross-sectional view of the actuator 20 taken along the line 3—3 of FIG. 2, shows in detail its internal construction. The main housing 22 has an internal annular recess 22a in which a rim 24a of the elastomer diaphragm 24 is disposed in sealing relationship, with the remainder of the diaphragm extending across a central opening 22b of the housing. As is clearly shown in FIGS. 3 and 4, the rim portion 24a of the diaphragm 24 is of reduced thickness with respect to the remainder of the diaphragm to facilitate its mounting in the annular recess 22a. The diaphragm 24 also has a central hole or bore 24b which receives a shank portion 28a of the push button 28. The diameter of the shank portion 28a of the push button 28 is greater than the inside diameter of the bore 24b in the diaphragm 24, and hence there is an interference fit resulting in sealing of the liquid within the interior of the actuator 20.

The elastomer diaphragm 24 also is compressed at its center to reduce its thickness in a vertical direction, as viewed in FIG. 3, because the length of the shank portion 28a of the push button 28 is shorter than the thickness of the diaphragm, hence causing a shoulder 32a of a valve poppet 32 to be forced against a bottom, center surface portion 24c of the diaphragm when a cap screw 30 is advanced into the push button 28. This compression of the elastomer diaphragm 24 causes enhanced sealing at its center as well as at the annular recess 22a of the housing 22 and, in fact, places the entire diaphragm 24 in severe compression, as shown in FIG. 3, for this purpose.

Because the push button 28 extends outward above an upper outer surface of the diaphragm 24, as viewed in FIG. 3, it can be readily felt under the skin 21 (FIG. 1) and is therefore easily found and hence readily depressed to operate the actuator 20.

When the penis P and the penile prosthesis 10 are in their flaccid state, an upper surface of a flange 32b of the poppet 32 is closed in contact with an "O"-ring seat 34 which is placed within an "O"-ring groove 22c of the housing 22. At that time, the pressure of the liquid in the prosthesis 10 which is upstream of the poppet 32, including the liquid occupying a lower chamber 44 of the actuator 20 and an annular passageway 48 in a bottom cover 46, is relatively high, and the pressure of the liquid downstream of the poppet, including the liquid in an upper chamber 50 of the actuator 20, is relatively low. Thus, when the push button 28 (and hence the poppet 32) is pushed downward, the seal between the flange 32b and the "O"-ring 34 is broken and the pressurized liquid is driven from the reservoir 12 (FIG. 1) through the tube 13, through an interior lumen 38 of the inlet port 36 into an entrance passageway 40 of the housing 22 and then through an opening 42 cut in the annular passageway 48 of the bottom cover 46. The fluid then passes over the depressed poppet flange 32b into the upper chamber 50 of the housing 22, through an exit passageway 52 of the housing, and then into an interior lumen 54 of the outlet port 56. Finally, the liquid enters and pressurizes the stiffener cylinders 60 that are shown in FIG. 1, thus causing the erect state P' of the penis P, as above described.

As viewed in FIG. 3, as soon as finger pressure is removed from the push button 28, an inherent upward spring force is exerted by the elastomer diaphragm 24, to move the depressed poppet flange 32b upward firmly and positively against the "O"-ring seat 34, to maintain the erect state P' of the penis P. This firm seating of the poppet flange 32b against the "O"-ring seat 34 by the upwardly directed spring force is a result of the interface between the lower surface 24c of the diaphragm 24 and the shoulder 32a of the poppet 32 being located at a level such that the diaphragm is always partially deflected inwardly or downwardly, even when the poppet flange engages the "O"-ring. Additional spring force for firmer seating can be obtained from the diaphragm 24 by decreasing the vertical height of the poppet 32, i.e., by further lowering the interface between the lower surface 24c of the diaphragm 24 and the shoulder 32a of the poppet 32.

When the flaccid state of the penis P and the penile prosthesis 10 are again desired, the push button 28 is depressed through the skin 21 (FIG. 1) of the user, thus opening the valve poppet 32 of the actuator 20 with respect to the "O"-ring 34. The penis P is then squeezed with the other hand causing the liquid to be driven back into the reservoir 12 (FIG. 1). When a sufficiently flaccid state of the penis P is obtained, the finger pressure is first removed from the skin 21 over the push button 28 and then the pressure on the penis is removed. At this point the liquid in the upper chamber 50 of the actuator 20 again is at a relatively low pressure and the liquid in the lower chamber 44 is at a relatively high pressure. More specifically, the liquid in the upper chamber 50 is typically at essentially zero pressure, and the liquid in the lower chamber 44 is at the pressure of the vapor pressure in the reservoir 12, which pressure is typically between 2 and 15 psig. The area of the upstream side of the poppet flange 32b, which is relatively large, multiplied by the difference in pressure between the lower chamber 44 and the upper chamber 50, then results in a force which also seals the flange 32b firmly and positively against the "O"-ring 34, thus preventing flow of the pressurized liquid back into the cylinders 60. This force, in combination with the upward spring force of the diaphragm 24 previously described, also precludes the inadvertent actuation of the system by accidental and transient pressure on the skin 21 over the site of the actuator 20 when the penis P is in its flaccid state.

Referring to FIG. 3, the elastomer diaphragm 24 and "O"-ring 34 of the actuator 20 are typically made from a biocompatible material such as medical grade silicone rubber, and all other parts are typically machined from a biocompatible material such as pure titanium metal or a biocompatible titanium alloy, such as 90% titanium, 6% aluminum and 4% vanadium. The outside diameter of the actuator 20 is typically between 1 and 4 inches and the thickness of the actuator is typically between 0.25 and 0.75 inches. Further, the inlet port 36 is typically joined to the housing 22 by a weld 37 and similarly each outlet port 56 is typically joined to the housing 22 by a weld 57. The bottom cover 56 also is joined along its outer circumference to the housing 22 by a weld 47 so as to be an integral part of the housing.

Figure 4:
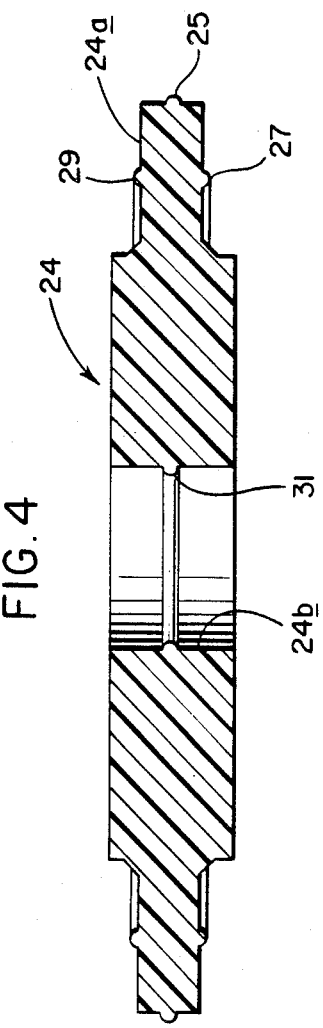
FIG. 4 is a detailed, cross-sectional view of an undeformed elastomer diaphragm of the flow control device.

FIG. 4 is a cross-sectional view showing details of the uncompressed diaphragm 24. The thickness of the diaphragm 24 is typically between 0.050 and 0.50 inch, and its outside diameter is between 0.5 and 2 inches. The reduced thickness rim 24a that fits into the recess 22a (see FIG. 3) includes three rings 25, 27 and 29 of semicircular cross section that are integrally molded with the elastomer rim around its periphery and on opposite sides thereof, respectively. Each semicircular ring 25, 27 and 29 provides a seal to prevent loss of fluid from within the actuator 20. Thus, the three semicircular rings 25, 27 and 29 cooperate to provide a triple seal. The cylindrical hole 24b at the center of the diaphragm 24 also includes at its midpoint an internal ring 31 of semicircular cross section that is integrally molded with the diaphragm and which provides a seal engaged against the shank portion 28a of the push button 28.

As is illustrated by broken lines in FIG. 3, a non-coring (Whitacre point) hypodermic needle 58 that penetrates the skin 21 (FIG. 1) and the compressed diaphragm 24 and which is attached to a syringe (not shown), can be used to add liquid to or remove liquid from the actuator 20 and thus the penile prosthesis 10 in a manner disclosed in my U.S. Pat. No. 4,559,931, the pertinent portion of which is hereby incorporated by reference. This is another unique feature of the present invention in that, since the required diaphraqm spring force and sealing action produced by the diaphragm 24 in accordance with the invention, is obtained by placing the entire diaphragm 24 in a state of high compression, the diaphragm also functions as an excellent, self-sealing septum having an enhanced self-sealing capability.

While the actuator 20 has been described herein in conjunction with the penile prosthesis 10, several features of this actuator design also can be used in any implantable prosthetic device or system which requires such design features; e.g., a manually actuated hydraulic urinary sphincter, as described in my copending application Ser. No. 831,950 being filed on even date with this application.

In summary, a new and improved flow control device in the form of the actuator 20 has been described, in which the valve poppet 32 is mounted directly on the elastomer diaphragm 24 for movement therewith. When the elastomer diaphragm 24 is deflected inward by manual pressure on the push button 28, the poppet 32 is moved to an open position, and when pressure on the push button 28 is released, the elastomer diaphragm moves the valve poppet back to a closed position with an inherent spring force to seat the poppet firmly on the "O"-ring seat 34. In a flaccid state, higher fluid pressure in the lower chamber 44 than in the upper chamber 50 further increases this seating force as a result of the relatively large area of the poppet flange 32b. The outward projection of the push button 28 makes it easy to find beneath the skin of the user, increasing the reliability of the actuator 20 and its ease of use. Reducing the central thickness of the elastomer diaphragm 20 by the push button-and-valve poppet securing screw 30 to place the diaphragm in high compression, together with the semicircular seals 25, 27, 29 and 31, increases the liquid-sealing capability of the diaphragm. The placing of the elastomer diaphragm 24 in high compression also enhances its self-sealing capability when it is penetrated by the hypodermic needle 58 for adding or removing liquid from the actuator 20.

Various other modifications, adaptations and alternative designs than those disclosed herein are, of course, possible in light of the above teachings. Therefore, it should be understood at this time that within the scope of the appended claims, the invention may be practiced otherwise than as specifically described herein.

What is claimed is:

1. For use with an implanted prosthesis, a flow control device comprising:
   a housing having an opening therein;
   an elastomer diaphragm disposed across the opening in the housing and having a peripheral portion mounted on the housing in fluid-tight relationship to an interior of the housing, the elastomer diaphragm being deflectable inward relative to the interior of the housing; and
   valve means in the housing for controlling the flow of fluid through the housing, the valve means including a valve member mounted on the elastomer diaphragm for movement with the diaphragm from a closed position to an open position as the diaphragm is manually deflected inward, and for movement with the diaphragm back to a closed position as the diaphragm returns to an original condition when manual pressure on the diaphragm is removed.

2. The flow control device recited in claim 1, further comprising an outwardly projecting push button mounted on an outer surface of the elastomer diaphragm essentially centrally thereof, for applying manual pressure to and deflecting the diaphragm.

3. The flow control device recited in claim 2, wherein the valve member is a valve poppet mounted on an inner surface of the elastomer diaphragm, the elastomer diaphragm has a central bore therethrough, a portion of one of the push button or the valve poppet extends through the bore in the diaphragm, and a securing means is provided for securing the push button and the valve poppet to one another and for compressing a portion of the diaphragm therebetween to provide a fluid-tight seal.

4. The flow control device recited in claim 3, wherein the securing means is a screw.

5. The flow control device recited in claim 2, further comprising means for securing the push button to the elastomer diaphragm and also compressing the elastomer diaphragm, the compressed diaphragm being self-sealing and capable of being penetrated by a hypodermic needle for the adding or removal of fluid from the device.

6. The flow control device recited in claim 1, wherein the elastomer diaphragm has a thickness in a range on the order of 0.050 to 0.50 inches and a diameter in a range on the order of 0.5 to 2.0 inches.

7. The flow control device recited in claim 1, wherein the flow control device has a diameter in a range on the order of 1 to 4 inches and a thickness in a range on the order of 0.25–0.75 inches.

8. The flow control device recited in claim 1, which further comprises means for reducing the thickness of the elastomer diaphragm centrally thereof and thereby compressing the remainder of the elastomer diaphragm, the compressed diaphragm being self-sealing and capable of being penetrated by a hypodermic needle for the adding or removal of fluid from the device.

9. For use with an implantable prosthesis, a flow control device capable of being implanted subcutaneously and comprising:

an annular housing having a central opening therein;
a single, thick elastomer diaphragm disposed in the central opening of the annular housing and having an annular rim of reduced thickness mounted in an internal annular recess in the annular housing;
an outwardly projecting push button having an annular head portion and a cylindrical shank portion of reduced diameter with respect to the head portion, the push button being mounted on an outer side of the diaphragm with the head portion engaged with the outer side and with the shank portion extending through a central bore in the diaphragm;
a fluid inlet port and a fluid outlet port connected to the housing;
passage means in the housing to permit flow of fluid through the housing from the inlet port to the outlet port;
an "O"-ring valve seat in the housing;
a valve poppet for precluding flow of fluid through the passage means when the valve poppet is in a closed position engaged with the "O"-ring valve seat, the housing having upstream and downstream chambers on opposite sides of the flange and the flange having a relative large area on the upstream side thereof so that a higher pressure in the upstream chamber forces the flange firmly against the valve seat;
a screw extending through the valve poppet and threaded into the shank portion of the push button, to secure the push button to the outer side of the elastomer diaphragm and the valve poppet to an inner side of the elastomer diaphragm, the screw being threaded into the shank portion so as to compress a portion of the elastomer diaphragm between the head portion of the push button and the valve poppet, to form a fluid seal; and
the elastomer diaphragm being inwardly deflectable in response to manual pressure exerted on the push button member, to move the valve poppet flange to the open position disengaged from the "O"-ring valve seat, and recovering to an original condition upon removal of manual pressure from the push button, to close the valve poppet flange against the "O"-ring valve seat, with an interface between the elastomer diaphragm and the valve poppet being located relative to the valve seat so that the diaphragm remains partially deflected when the flange is engaged with the seat.

10. The flow control device recited in claim 9, further comprising an annular seal of semicircular cross section integrally formed with the elastomer diaphragm in the central bore thereof.

11. The flow control device recited in claim 10, further comprising annular seals of semicircular cross section integrally formed with the annular rim of the elastomer diaphragm on a peripheral surface and opposite sides of the rim, respectively.

12. The flow control device recited in claim 11, wherein the device is formed entirely of biocompatible materials and is capable of being implanted subcutaneously, the device has a diameter in a range on the order of 1 to 4 inches and a thickness in a range on the order of 0.25–0.75 inches, the elastomer diaphragm has a thickness in a range on the order of 0.050 to 0.50 inches and a diameter in a range on the order of 0.5 to 2.0 inches, and the elastomer diaphragm is capable of being penetrated by a non-coring hypodermic needle for adding or removing fluid from the device.

13. The flow control device recited in claim 9, further comprising at least one annular seal of semicircular cross section integrally formed with the annular rim of the elastomer diaphragm.

14. The flow control device recited in claim 9, further comprising annular seals of semicircular cross section integrally formed with the annular rim of the elastomer diaphragm on a peripheral surface and opposite sides of the rim, respectively.

15. An implantable penile erection device, comprising:

a reservoir containing a vapor pressure driven fluid;
a pair of fluid filled elastomer cylinders capable of being mounted in the corpora cavernosa of a penis;
a fluid flow control device disposed between the reservoir and the fluid filled elastomer cylinders, the fluid flow control device including a housing having an opening therein;
an elastomer diaphragm disposed across the opening in the housing and having a peripheral portion mounted on the housing in fluid-tight relationship to an interior of the housing, the elastomer diaphragm being deflectable inward relative the interior of the housing;
valve means in the housing for controlling the flow of fluid through the housing, the valve means including a valve member mounted on the elastomer diaphragm for movement with the diaphragm from a closed position to an open position as the diaphragm is manually deflected inward, and for movement with the diaphragm back to a closed position as the diaphragm returns to an original condition when manual pressure on the diaphragm is removed; and
means for interconnecting the reservoir, housing and the cylinders.

16. For use with an implanted prosthesis, a flow control device comprising:
 a housing having an opening therein;
 an elastomer diaphragm disposed across the opening in the housing and having a peripheral portion mounted on the housing in fluid-tight relationship to an interior of the housing, the elastomer diaphragm being deflectable inward relative to the interior of the housing; and
 valve means in the housing for controlling the flow of fluid through the housing, the valve means including a valve member mounted on the elastomer diaphragm for movement with the diaphraqm from a closed position to an open position as the diaphragm is manually deflected inward, and for movement with the diaphragm back to the closed position as the diaphragm returns to an original condition when manual pressure on the diaphragm is removed, and the valve means further including a valve seat engageable by the valve member, with an interface between the inner side of the elastomer diaphragm and the valve member being located relative to the valve seat so that the elastomer diaphragm remains partially deflected inward when the valve member is engaged with the valve seat.

17. The flow control device recited in claim 16, wherein the valve member includes a flange for engaging the valve seat, the housing includes upstream and downstream chambers on opposite sides of the valve member flange, and the flange has a relatively large area on an upstream side thereof so that a relatively high fluid pressure in the upstream chamber cooperates with the elastomer diaphragm to force the flange firmly against the valve seat.

18. For use with an implanted prosthesis, a flow control device comprising:
 a housing having an opening therein;
 an elastomer diaphragm disposed across the opening in the housing and having a peripheral portion mounted on the housing in fluid-tight relationship to an interior of the housing, the elastomer diaphragm being deflectable inward relative to the interior of the housing; and
 valve means in the housing for controlling the flow of fluid through the housing, the valve means including a valve poppet mounted on an inner surface of the elastomer diaphragm for movement with the diaphragm from a closed position to an open position as the diaphragm is manually deflected inward, and for movement with the diaphragm back to a closed position as the diaphragm returns to an original condition when manual pressure on the diaphragm is removed;
 an outwardly projecting push button mounted on an outer surface of the elastomer diaphragm essentially centrally thereof, for applying manual pressure to and deflecting the diaphragm, the elastomer diaphragm having a central bore therethrough, and a portion of one of the push button or the valve poppet extending through the bore in the diaphragm;
 a securing means for securing the push button and the valve poppet to one another and for compressing a portion of the diaphragm to provide a fluid-tight seal; and
 an annular seal of semicircular cross section integrally formed with the elastomer diaphragm in the central bore thereof.

19. For use with an implanted prosthesis, a flow control device comprising:
 a housing having an opening therein;
 an elastomer diaphragm disposed across the opening in the housing and having a peripheral portion mounted on the housing in fluid-tight relationship to an interior of the housing, the elastomer diaphragm being deflectable inward relative to the interior of the housing, the housing including an annular internal recess surrounding the opening in the housing, and the periphery of the elastomer diaphragm being an annular rim of reduced thickness mounted in the internal recess; and
 valve means in the housing for controlling the flow of fluid through the housing, the valve means including a valve member mounted on the elastomer diaphragm for movement with the diaphragm from a closed position to an open position as the diaphragm is manually deflected inward, and for movement with the diaphragm back to a closed position as the diaphragm returns to an original condition when manual pressure on the diaphragm is removed.

20. The flow control device recited in claim 19, further comprising at least one annular seal of semicircular cross section integrally formed with the rim of the elastomer diaphragm.

21. The flow control device recited in claim 19, further comprising annular seals of semicircular cross section integrally formed with the annular rim of the elastomer diaphragm on a peripheral surface and opposite sides of the rim, respectively.

* * * * *